United States Patent [19]

Miller

[11] Patent Number: 4,857,061
[45] Date of Patent: Aug. 15, 1989

[54] SINGLE-FLOW VALVE-HYPODERMIC NEEDLE COMBINATION

[76] Inventor: Michael D. Miller, 287 Dartmouth St., Rochester, N.Y. 14607

[21] Appl. No.: 181,835

[22] Filed: Apr. 15, 1988

[51] Int. Cl.$^4$ .............................................. A61M 5/00
[52] U.S. Cl. ..................................... 604/207; 604/246
[58] Field of Search ............... 604/207, 187, 190, 236, 604/246, 247; 137/527, 529, 535, 537

[56] References Cited

U.S. PATENT DOCUMENTS

| | | |
|---|---|---|
| 3,557,778 | 1/1971 | Hughes . |
| 3,572,556 | 3/1971 | Pogacar ............................. 604/207 |
| 3,951,146 | 4/1976 | Chiquiar-Arias . |
| 4,066,079 | 1/1978 | Chiarolla ............................. 604/190 |
| 4,233,975 | 11/1980 | Yerman . |
| 4,643,723 | 2/1987 | Smit ..................................... 604/207 |

*Primary Examiner*—John D. Yasko
*Attorney, Agent, or Firm*—Cumpston & Shaw

[57] ABSTRACT

A single flow valve is disclosed for use in a hypodermic needle. The flow valve comprises a valve chamber interposed between the needle and a syringe connector, and valve means mounted within the valve chamber. The valve means controls fluid flow through the valve chamber to a single-shot of fluid in one direction, and has a normal partially tensioned position, an optimum tensioned position on one side of the normal partially tensioned position, and a latched closed position on the opposite side of the normal partially tensioned position. The valve means is movable to its optimum tensioned position in response to fluid flow through the valve chamber in the one direction. The valve means is movable from the optimum tensioned position to its latched closed position in response to the inherent tension therein when the flow of fluid is abated. In the latched closed position, further fluid flow through the valve chamber in the one direction is prevented.

44 Claims, 7 Drawing Sheets

SINGLE-FLOW VALVE-HYPODERMIC NEEDLE COMBINATION

BACKGROUND OF THE INVENTION

1. Field of the Invention:

The present invention relates generally to single flow valves, and more particularly to a single-flow valve for use in a hypodermic needle.

2. Description of the Prior Art:

The re-use of needles by intravenous drug abusers, a group that numbers approximately 750,000 nationally, results in various infections, including hepatitis, and AIDS (Acquired Imuno deficiency Syndrome).

Hepatitis is believed to be widespread among the drug addict population, whose dirty needles spread the disease from one addict to another. While hepatitis has heretofore been considered to be a suburban problem, such has proven otherwise as large numbers of cases of hepatitis have been in found in urban and rural areas.

In regard to the AIDS disease, while it was initially confined mostly to certain sub-sets of the general population, namely homosexuals and drug addicts, the AIDS virus is now beginning to spread into the general population. The main force behind this spread of AIDS appears to be the intravenous drug abusers. As the Commissioner of the New York State Department of Health, Stephen C. Joseph, M.D., M.Ph. reports, "The spread of the AIDS virus will not be slowed, nor will its seepage into the heterosexual community be prevented, without a meaningful war on drugs. The future of the epidemic lies with the connection between AIDS and the intravenous drug abuser."

The degree to which the AIDS epidemic has spread is uncertain. Estimates vary widely, but there is agreement that the AIDS epidemic is spreading and that the costs to society, in terms of dollars spent and productivity lost, will continue to rise exponentially into the coming decade. Various estimates of these costs that have appeared in journals and periodicals include: $1 billion in the U.S. in 1987; Annual U.S. AIDS costs of $66.4 billion by 1991; New York cost of $2 billion in 1991; 100 million individuals exposed by 1990; seven-fold increase in cases from heterosexual transmission by 1990; and 120,000 to 270,000 cumulative cases in the U.S. by 1991. A British District's study projects AIDS to surpass heart disease as the leading cause of life years lost by 1990.

The attack on AIDS has been multi-directional, namely testing, treatment, vaccine, education and prevention.

In regard to testing, testing methods have been developed and are in place, but questions remain as to their absolute effectiveness. New strains of the virus, and the time lag between infection and antibody formation have raised concern that present testing methods are inadequate.

In regard to treatment, treatment regimens are being developed very aggressively, but hopes are a "cure" soon are small. Controlling symptoms and reducing infectivity are more likely outcomes.

In regard to vaccine production, which is the traditional method of choice to combat viral diseases, progress has been slow. *Journal of the American Medical Association* recently reported, in essence, that it was predicted a year ago that it would take a minimum of five years to develop a vaccine against HIV (AIDS virus), and that things today are even bleaker.

In regard to education, it is in the process of being expanded, particularly centering around the disease itself and preventing its spread. Although many myths and misconceptions still exist, increasingly the facts are being disseminated. The effectiveness of education towards changing behavior is also a concern.

In regard to the prevention of AIDS, for the general public and homosexual sub-population, prevention involves the practice of "safe sex". Prevention for the intravenous drug abuser means the use of sterile needles. Although new needles are packaged sterily, and intended for single use, intravenous drug users routinely re-use needles. While the "safe" practice of one user always using the same needle is fine in theory, this happens only infrequently at best.

Our understanding of the behavior patterns governing intravenous drug abusers' needle sharing is inadequate. There are inherent problems in data collection involving this illegal activity. It is known that needle sharing has been previously associated with the communal ritual of drug use, and that intravenous drug users, when experiencing withdrawal, will use whatever means is at hand to administer the drugs.

As a result of the serious problem presented by the AIDS epidemic, there has been an increased demand for clean needles with several resultant market responses. In the New York City area, sellers of the drugs are including two new needles with every purchase, instead of the standard one, and there has been an emergence of the repackaging of needles and selling them as new. Long term results of this practice are unpredictable, but potentially catastrophic. Accordingly, preventing re-use of needles would help contain the spread of AIDS, as well as reduce the incidence of any other infectious diseases, such as hepatitis, which are spread through intravenous drug abuse.

The application of this invention to hypodermic needles would change needles that are currently intended for single use, into those that in fact can only be used a single time. In theory, if such needles were exclusively used, the exposure of new individuals to AIDS, and other diseases, via blood routes, would be virtually eliminated, and an entire avenue of transmission would be eliminated. While this change in needle design would not eliminate the use of currently existing dirty needles, through needle exchange programs, clean non-reuseable needles would systematically replace unsterile needles currently in use at a rate restricted only by the success of such programs, and the continued availability of needles susceptible to abuse.

In regard to the patented art, a single-use syringe is disclosed in U.S. Pat. No. 3,951,146, which issued to Chiquiar-Arias on April 20, 1976. This patent is directed to a blade-containing syringe, which self-destructs upon a pressing of the plunger thereof during the expelling of the syringe contents. Also, U.S. Pat. No. 4,233,975, which issued to Yerman on Nov. 18, 1980, is directed to an anti-drug abuse single-use syringe having a plug member adapted to be pushed into a position blocking flow to and from the needle passage as the plunger's proximal portion is moved inwardly to expel the syringe contents. In the blocking position, the plug member is locked into a female member positioned to permit movement of the plug member to the blocking position, but preventing withdrawal of the plug member from the blocking position, thereby preventing subsequent intake or outflow through the syringe needle passage. The use of valve means is further disclosed in U.S. Pat. No. 3,557,778, which issued to Hughes on Jan. 26, 1971. The Hughes patent is directed to a blood specimen collection assembly, having a fluid inlet and a fluid outlet with valve means disposed within the assembly for movement to and from an open and closed positions. The valve means prevents the backflow of testing fluid from the specimen receptacle into the patient's bloodstream during use of the blood specimen collection assembly.

SUMMARY OF THE INVENTION

A broad object of the present invention is to provide a single-flow valve comprising:

a valve chamber;

valve means mounted within the valve chamber for movement between an open position in response to fluid flow through the vlave chamber, and a latched closed position for at least substantially preventing fluid flow through the valve chamber;

latch means forming a part of the valve means for latching the valve means in the latched closed position; and potential energy generating means forming a part of the valve means and responsive to the fluid flow through the valve chamber for storing potential energy for biasing the valve means to the latched closed position when the flow of fluid through the valve chamber is abated.

Another object of the present invention is to provide an improved single-flow valve for use in a hypodermic needle, which assures that the needle can be used only a single time, and one time only. The single-flow valve comprises:

a valve chamber; and valve means mounted within the valve chamber for controlling solution flow through the chamber to a single shot of solution in one direction, the valve means having an optimum tensioned position and a latched closed position, and is movable to its optimum tensioned position in response to the flow of the single-shot of solution through the valve chamber in the one direction, and is movable from its optimum tensioned position to its latched position in response to the tension therein when the flow of solution is abated whereby further solution flow in the one direction through the valve chamber is prevented.

In a more specific object of the invention, the valve means comprises a main valve flap having a normal partially tensioned position, the main valve flap being pivotal about one end and having an opposite free end. Control means are provided responsive to the force of the flow of solution for changing the position of the one end, and moving the main valve flap to its optimum tensioned position. When the flow of solution is abated, and the main valve flap is moved by the inherent tension or potential energy therein from its optimum tensioned position to its latched closed position, latch means are provided for latching the free end of the main valve flap in its latched closed position.

In a more specific object of the invention, the valve means comprises means for mounting one end of the main valve flap to the valve chamber, the mounting means comprising a first over-center leaf spring having a normal first over-center position, a second over-center position and a mid-portion to which the one end is secured.

Still another object of the invention is to provide an improved single flow valve, in which the control means comprise a cam member enagageable by the free end of the main valve flap which is adapted, upon initiation of the flow of solution, to force the first over-center leaf spring to its second over-center position.

Still another object of the present invention is to provide an improved single flow valve in which the valve means comprises a second spring having one end connected to the main valve flap, and the opposite end thereof connected to the valve chamber for biasing the main valve flap towards its latched closed position.

Still another object of the invention is to provide an improved single flow valve in which the control means further comprises a third over-center leaf spring coupled to the first over-center leaf spring. Upon initiation of the flow of solution, the third over-center leaf spring is moved over-center to assist movement of the first over-center leaf spring to its second over-center position.

Still another object of the present invention is to provide a single-flow valve wherein one of the main valve flap and mounting means is provided with a one-way flap valve for allowing solution flow through the valve chamber in the opposite direction.

In a more specific object of the present invention, a single flow valve is provided wherein the valve means comprises dual identical first and second valve means mounted within the valve chamber in 180° spaced or minor image relation for allowing solution flow through the valve chamber in either direction only once.

Still another object of the present invention is to provide a single flow valve wherein lock means are provided for releasably locking the main valve flap in its normal partially tensioned position. The lock means is released upon movement of the main valve flap to its optimum tensioned position in response to solution flow. The lock means comprises a lock plate pivotally secured about one end to the valve chamber, and having a laterally extending lug on the opposite end thereof. A fourth spring has one end thereof secured to the valve chamber and the opposite end thereof secured to the lock plate for biasing the lock plate into locking engagement with a laterally extending lip on the main valve flap.

BRIEF DESCRIPTION OF THE DRAWINGS

In the detailed description of the invention presented below, reference is made to the accompanying drawings, in which.

DETAILED DESCRIPTION OF THE PREFERRED EMBODIMENTS

While hypodermic syringes, including valves and needles, are well-known, the present description will be directed in particular to elements forming part of, or cooperating directly with, apparatus in accordance with the present invention. It is to be understood that elements not specifically shown or described may take various forms well-known to those skilled in the art.

Figure 1:
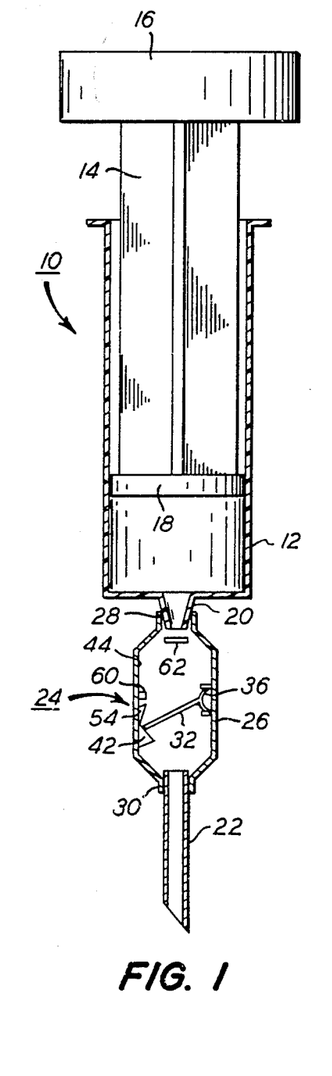
FIG. 1 is an elevational view in section of a syringe connected to a hypodermic needle in which a preferred embodiment of a single flow valve of this invention is incorporated.

With reference to FIG. 1, a hypodermic syringe 10 is disclosed comprising a tubular fluid or solution container 12 within which a reciprocally movable plunger 14 is mounted having a handle 16 at one end and a piston 18 on the other end. The tubular container 12 has a funnel-shaped outlet 20 which is normally connected to one end of a needle 22 by mating tapered fittings, a Luer lock or the like, not shown, as is well-known in the art. A preferred embodiment of a single-flow valve means 24 of this invention is mounted within a valve chamber 26 interposed between solution container outlet 20 and needle 22. The single-flow valve means 24 allows a single shot of solution to be directed through the needle, the valve means then moving to its latched closed position, so that it is impossible to reuse the needle.

Figure 2:
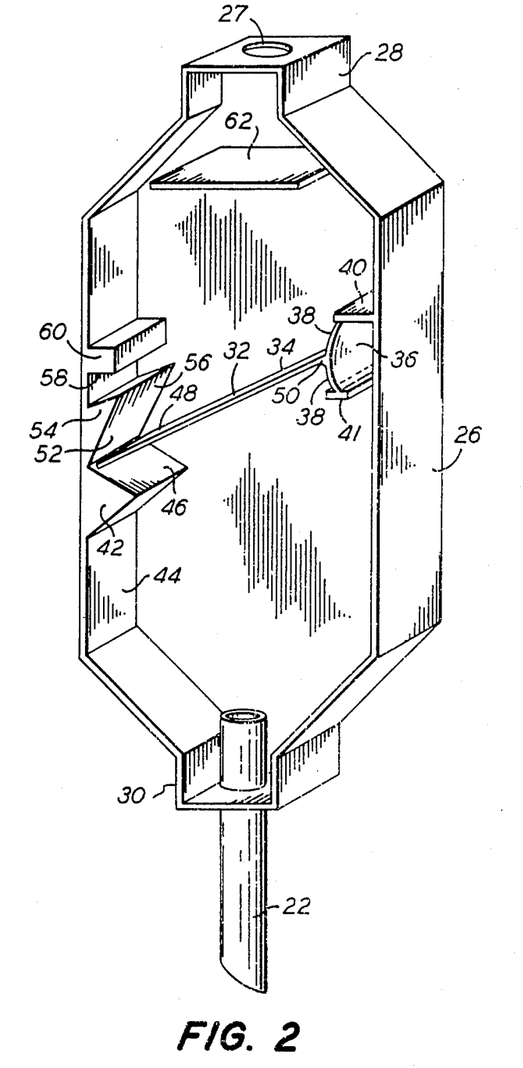
FIG. 2 is an enlarged perspective view of the single-flow valve of FIG. 1 with the front wall of the valve chamber removed to show a preferred embodiment of the valve means therein.

With reference to FIG. 2, a preferred embodiment of the valve means 24 of FIG. 1, in enlarged form, is mounted within valve chamber 26. The chamber has an inlet 27 in an upper collar 28 which receives the solution container outlet 20, and a lower collar 30 which is preferably permanently secured to one end of needle 22. The valve means 24 comprises a main valve flap 32 having one end 34 pivotally secured to the mid portion of a first over-center leaf spring 36 about a pivot 50. The ends 38 of leaf spring 36 are preferably integrally connected with valve chamber support members 40 and 41. Alternatively, edges 38 of leaf spring 36 may bottom into grooves, not shown, in support members 40 and 41. Preferably, support member 40 blocks the flow path behind leaf spring 36.

The valve means 24 is further provided with control means comprising a cam member 42 mounted on inner wall 44 of valve chamber 26. The cam member 42 has a slanted surface 46 engagable by a free end 48 of valve flap 32 for forcing or inverting over-center spring 36, shown in its normal first over-center position in FIGS. 2 and 4 to a second over-center position, shown in FIG. 5. In this second over-center position pivot 50 has been laterally moved outwardly. This interaction between free end 48 of main valve flap 32 and slanted surface 46 of cam member 42 is achieved as a single-shot of solution is forced by plunger 14 in the direction of arrow A, shown in FIG. 5. The force of the solution flow not only moves or inverts first over-center spring 36 to its second over-center position, but it also moves main valve flap 32 into an optimum tensioned or potential energy position. When the solution flow is abated or terminated, force tending to move the solution through needle 22 reduces towards zero and the tensioned main valve flap 32 is pivoted about pivot 50 by the inherent tension or potential energy therein in a clockwise direction, causing free end 48 thereof to clear cam member 42 and only partially engage a ramp guide surface 52 of a partially flexible catch member 54 mounted on inner wall 44 of valve chamber 26. The free end 48 of main valve flap 32 is guided by ramp guide surface 52 over a tooth portion 56 thereof, and into a latched closed position between tooth portion 56 and a bottom surface 58 of a stop member 60 mounted on the inner wall 44 of valve chamber 26. In this latched closed position, free end 48 of main valve flap 32 is captured between tooth position 56 and stop member 60, as seen in FIG. 6.

Figures 3, 4, 5, 6:
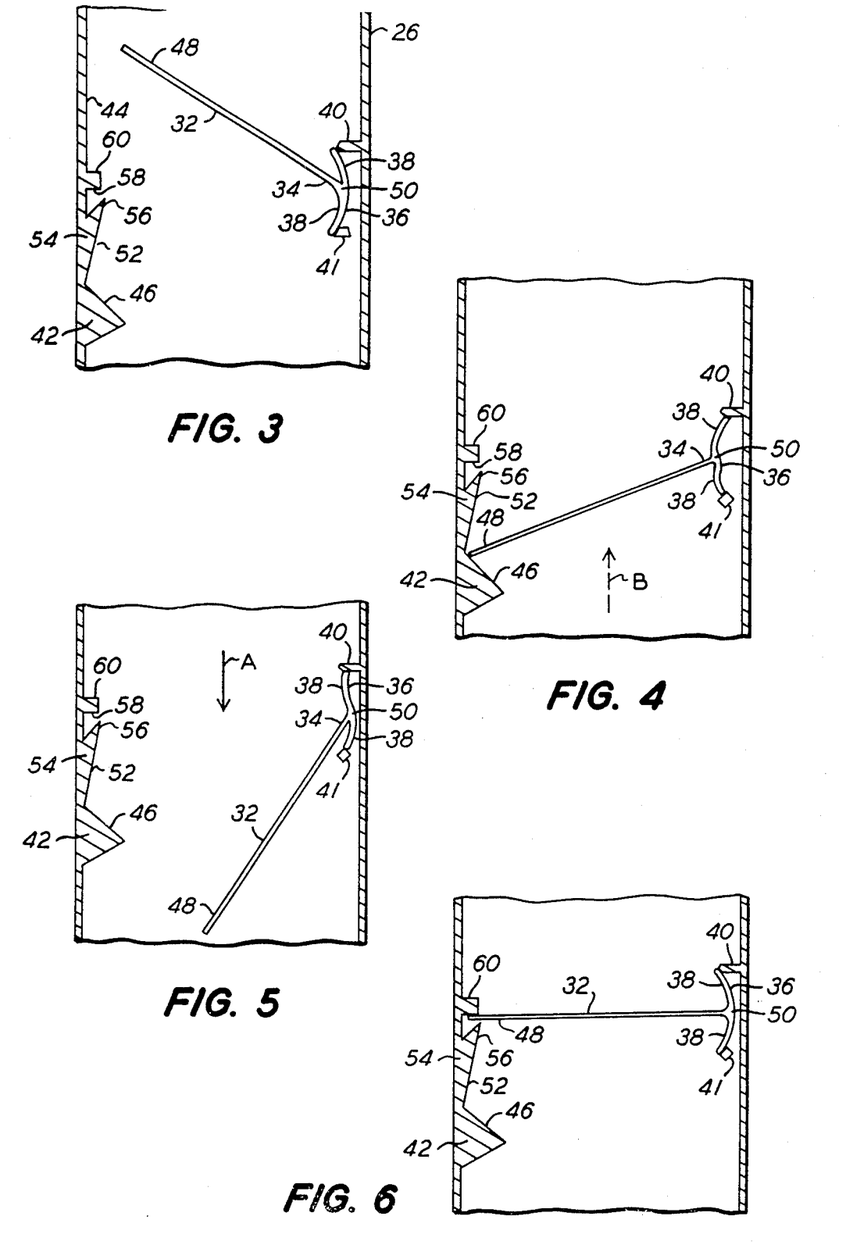
FIG. 3 is a segmental elevational view in section showing the valve means of FIG. 2, in which the main valve flap is in a neutral-energy position.
FIG. 4 is a segmental view similar to FIG. 3 showing the main valve flap of the valve means in a normal partially tensioned position between the optimum tensioned position and the latched closed position.
FIG. 5 is a segmental view similar to FIG. 3 showing the main valve flap of the valve means in its optimum tensioned position in response to solution flow.
FIG. 6 is a segmental view similar to FIG. 3 showing the main valve flap of the valve means in its latched closed position.

The tension in main valve flap 32 is obtained by integrally connecting one end 34 of main valve flap 32 to the mid-portion of first over-center spring 36 so that the main valve flap has a neutral energy position, substantially as seen in FIG. 3. When valve means 24 is manufactured, main valve flap 32 is moved from its neutral energy position into its normal partially tensioned position, as seen in FIG. 4. Such pivotal movement of main valve flap 32 is believed to flex over-center spring 36 which places valve flap 32 under partial tension. However, this partial tension is insufficient to force free end 48 of main valve flap 32 over ramp grid surface 52 into its latched closed position.

The size of cam member 42 and angle of surface 46 are preferably selected so that inversion of second over-center spring 36 geometrically occurs before flow occurs in direction A.

It is possible to go directly from the normal partially tensioned position of FIG. 4 to the latched closed position of FIG. 6 if solution flow is in a reverse direction indicated by a broken arrow B in FIG. 4. In this case, free end 48 of main valve flap 32 would be forced by solution flow into engagement with guide surface 52 causing first over-center spring 36 to invert. The increased energy in spring 36 along with the force of the solution flow would move main valve flap 32 into its latched closed position, seen in FIG. 6.

Preferably, blocking plate 62 is mounted within the upper end of the valve chamber 26 to prevent the possibility of anyone tampering with valve means 24 by inserting a foreign object, such as a nail, through inlet 27 of valve chamber 26 into engagement with main valve flap 32 releasing it from its latched closed position or otherwise disabling it.

Figures 7, 8, 9, 10:
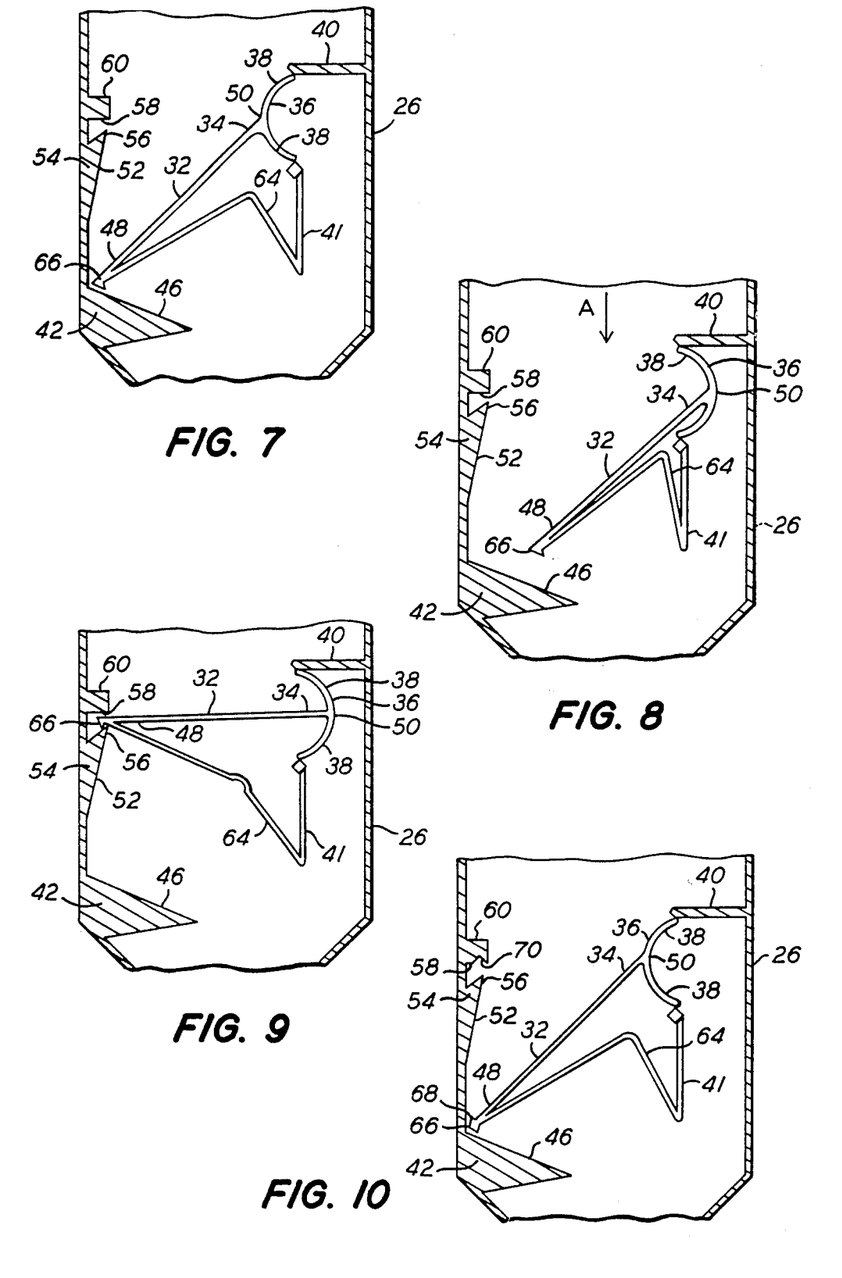
FIG. 7 is a view similar to FIG. 3 showing another embodiment of the single-flow valve of this invention with the main valve flap in its normal partially tensioned position.
FIG. 8 is a view similar to FIG. 7 showing the main valve flap in its optimum tensioned position in response to solution flow.
FIG. 9 is a segmental view similar to FIG. 7 showing the main valve flap in its latched closed position.
FIG. 10 is a segmental view similar to FIG. 7 showing the main valve flap of the valve means with an improved latch.

With reference to other embodiments of valve means 24 of this invention to be described hereinafter, is shown in which parts thereof similar to parts disclosed in FIGS. 1-6 will be denoted by the same numerals. With reference to the embodiment disclosed in FIGS. 7-9, a V-shaped leaf spring 64 is provided having one end secured to free end 48 of main valve flap 32 and the opposite end thereof secured to fixed support member 41 of valve chamber 26. In the normal partially tensioned position of valve flap 32, shown in FIG. 7, second leaf spring 64 is partially tensioned, and is further compressed and tensioned as solution flow in the direction of arrow A substantially simultaneously moves valve flap 32 into its optimum tensioned position, and first over-center spring 36 into its over-center position, seen in FIG. 8. When the solution flow is terminated, the increased tension within the compressed leaf spring 64 moves main valve flap 32 into its latched closed position about new pivot 50, as seen in FIG. 9. In this FIGS. 7-9 embodiment, second leaf spring 64 can be the sole source of tension or potential energy, or it can operate in conjunction with the tension developed by an integral connection between main valve flap 32 and first over-center spring 36, discussed with reference to FIGS. 1-6. Also, in this embodiment, free end 48 of main valve flap 32 is provided with a laterally extending lip 66 for engaging toothed portion 56 of catch member 54 for more reliably securing the free end of main valve flap in its latched closed position, as best seen in FIG. 9.

Figures 11, 12, 13, 14:
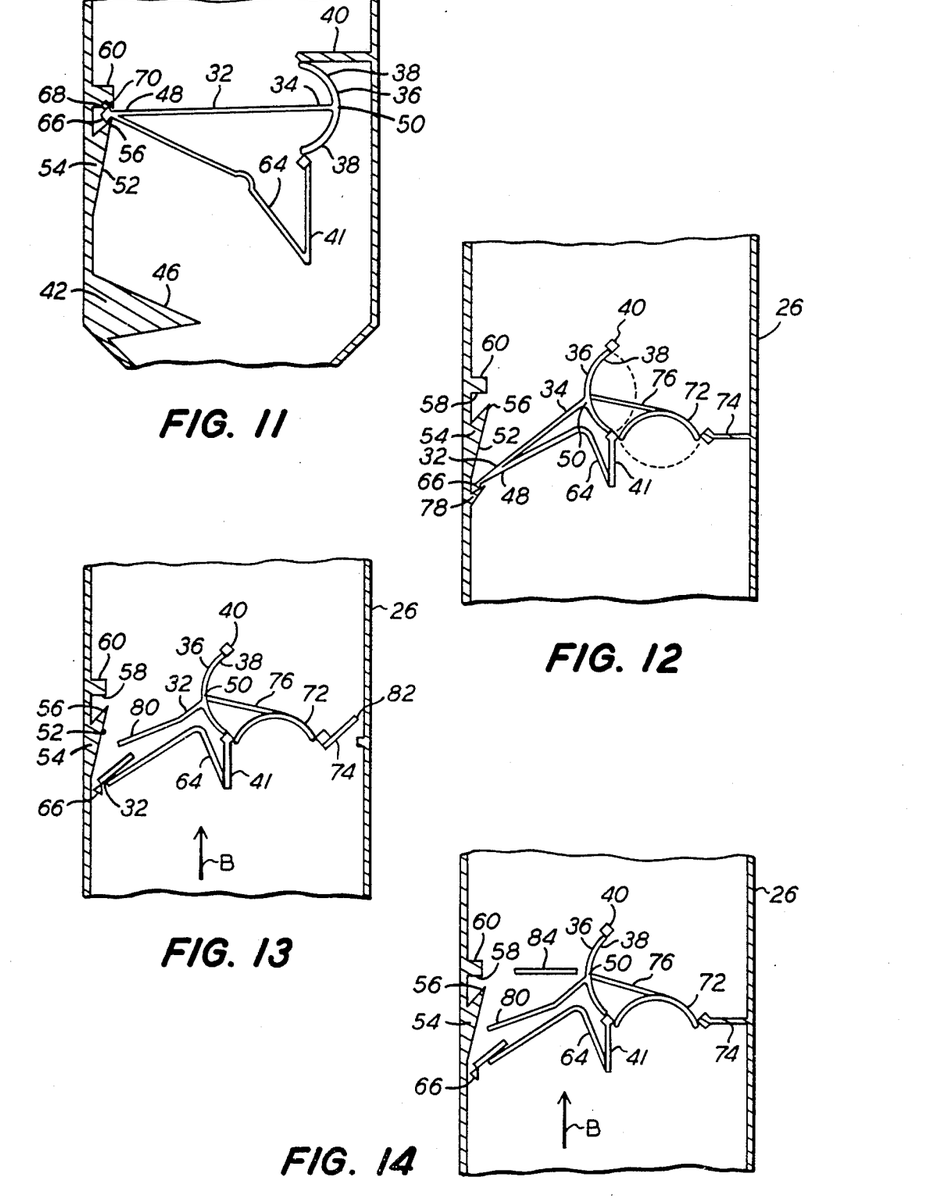
FIG. 11 is a segmental view similar to FIG. 10 showing the main valve flap in its improved latched closed position.
FIG. 12 is a segmental view similar to FIG. 7 of another embodiment of the valve means of this invention with the main valve flap in its normal partially tensioned position.
FIG. 13 is a segmental view similar to FIG. 12 showing the valve means with one-way valves for allowing solution flow in the opposite direction.
FIG. 14 is a segmental view similar to FIG. 13 in which a one-way valve allowing solution flow in the opposite direction engages and is closed by a stop member when the main valve flap is moved into its latched closed position.

With reference to FIGS. 10 and 11, free end 48 of main valve flap 32 of the valve means disclosed in FIGS. 7-9 is further provided with a laterally extending lip 68 opposite lip 66. The lip 68 engages a complementary groove 70 in bottom surface 58 of stop member 60 for more securely holding main valve flap 32 in its latched closed position.

With reference to FIGS. 12, 13 and 14, another embodiment of valve means 24 of this invention is disclosed in which a third over-center leaf spring 72, similar to first over-center leaf spring 36, is mounted between valve chamber support members 41 and 74 to assist movement of first over-center leaf spring 36 into its second over-center position. In this FIGS. 12-14 embodiment, the force of the solution flow against main valve flap 32 and third over-center spring 72 will force springs 36, 72 into the dotted positions shown in FIG. 12. During such movement, third spring 72 assists pulling first spring 36 into its over-center position by means of a linking member 76 coupling the first ands third over-center springs together. Also, in this embodiment, cam member 42 may be omitted, and a catch member 78 substituted therefor (FIG. 12) for holding main valve flap 32 in its normal partially tensioned position, or the cam member 42 can be omitted entirely (FIGS. 13 and 14).

Further, with reference to FIGS. 13 and 14, the valve means disclosed in FIG. 12 is further provided with one-way flap valves 80, 82, for allowing solution flow in the reverse direction of arrow B, opposite to the aforementioned forward direction of arrow A. The one-way flap valve 80 is located in main valve flap 32, and one-way flap valve 82 is located in one of the over-center spring support members 74. In the FIG. 13 embodiment, solution flowing in the reverse direction of arrow B can occur in any position of main valve flap 32. In the FIG. 14 embodiment, a stop plate member 84 is mounted in valve chamber 26 substantially in the plane of bottom surface 58 of stop member 60 for engaging and holding one-way flap valve 80 in its closed position when main valve flap 32 is moved into its latched closed position. Accordingly, in this embodiment, solution flow in the reverse direction, indicated by arrow B, is not possible when main valve flap 32 is in its latched closed position.

Figures 15, 16, 17, 18:
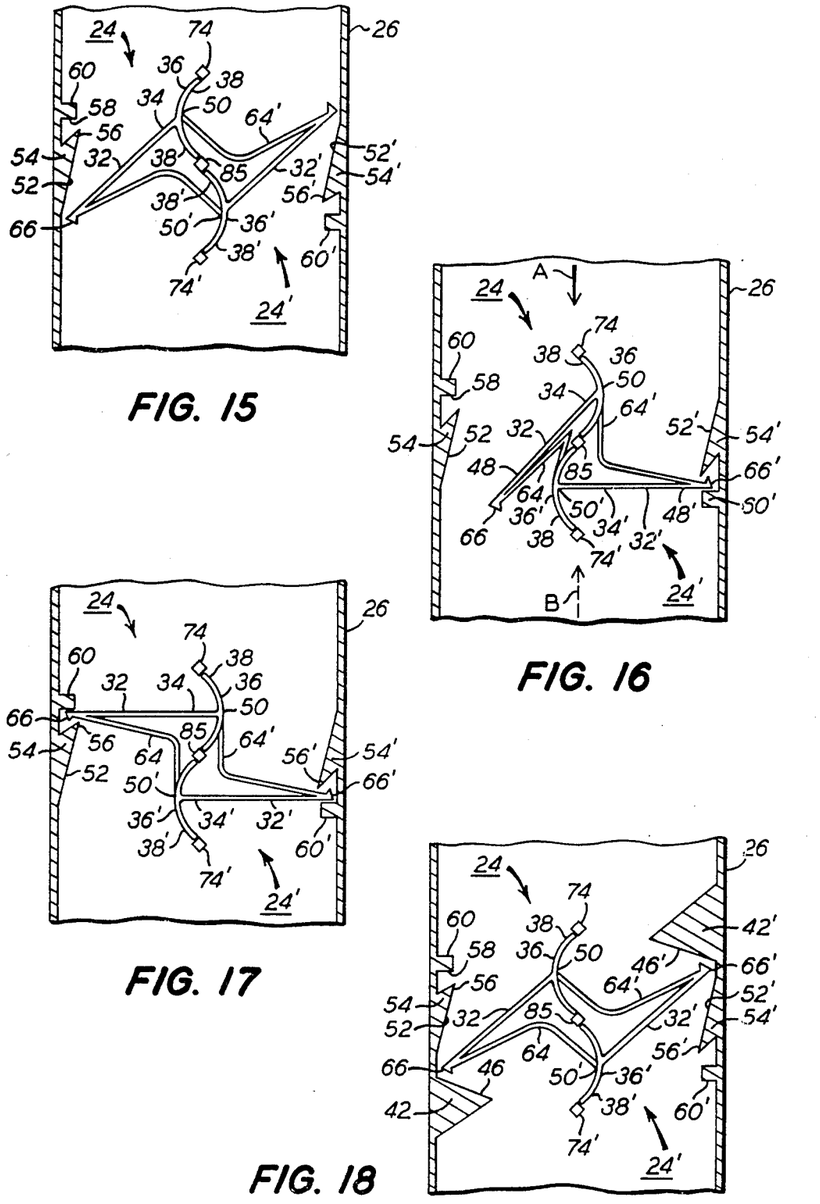
FIG. 15 is a segmental view similar to FIG. 7 showing another embodiment of the valve means of this invention in which identical dual valve means are mounted in a 180 degree out-of-phase or mirror image relation for allowing solution flow in either direction only one time.
FIG. 16 is a segmental elevational view of the dual valve means of FIG. 15 wherein the main valve flap of one of the valve means is in its optimum tensioned position and the other valve means is in its latched closed position.
FIG. 17 is a segmental view similar to FIG. 16 in which both of the dual main valve means are in their latched closed positions.
FIG. 18 is a segmental view similar to FIG. 15 in which the dual valve means are provided with cam members to assist movement of the over-center leaf springs to their opposite over-center positions.

With reference to the embodiment of the invention disclosed in FIGS. 15, 16 and 17, dual valve means are provided, each similar to the valve means 24 disclosed in FIG. 7 for selectively allowing a single solution flow either in the forward direction designated by arrow A, or in the reverse direction designated by arrow B. Since the dual valve means 24 are identical, for purposes of clarity, one of the valve means will be designated by the same numerals designated heretofore, and the other valve means will be designated by the same numerals primed. The dual valve means are but arranged in mirror image or 180° spaced relation with one another so that one valve means 24 functions to control solution flow in direction A, whereas the other valve means 24' functions to control solution flow in direction B. In this FIGS. 15–17 embodiment, the first over-center springs 36, 36' of the dual valve means have ends 38, 38' secured to a common fixed post 85, the opposite ends 38, 38' being connected to support members 74, 74'. One end of each of the second V-shaped leaf springs 64, 64' is connected to the mid-portion of the first over-center leaf spring 36, 36' of the other valve means. Accordingly, when the solution flow is directed through valve means 24 in the forward direction of arrow A, as seen in FIG. 16, one of the main valve flaps 32' is moved to its latched closed position for directly moving its associated first over-center spring 36' to its over-center position, and further causing leaf spring 64' to relax allowing the first over-center spring 36 of the main valve flap 32 to offer less resistance to movement to its over-center position. Accordingly, movement of the first over-center leaf springs 36, 36' into their other over-center positions, as seen in FIG. 16, possibly reduces the tension of the second leaf spring 64' associated with the closed main valve flap 32' and increases the tension of the tensioned second leaf spring 64 associated with the open main valve flap 32 for assuring movement of the optimum tensioned main valve flap 32 into its latched closed position, seen in FIG. 17.

The embodiment of the invention shown in FIG. 18 is essentially the embodiment disclosed in FIGS. 15–17 modified by incorporating therein cam members 42, 42'. The cam members assist movement of the first over-center springs 36, 36' into their second over-center positions upon solution flow in either direction for moving a selected main flap 32, 32' into its fully tensioned position.

Figures 19, 20, 21, 22:
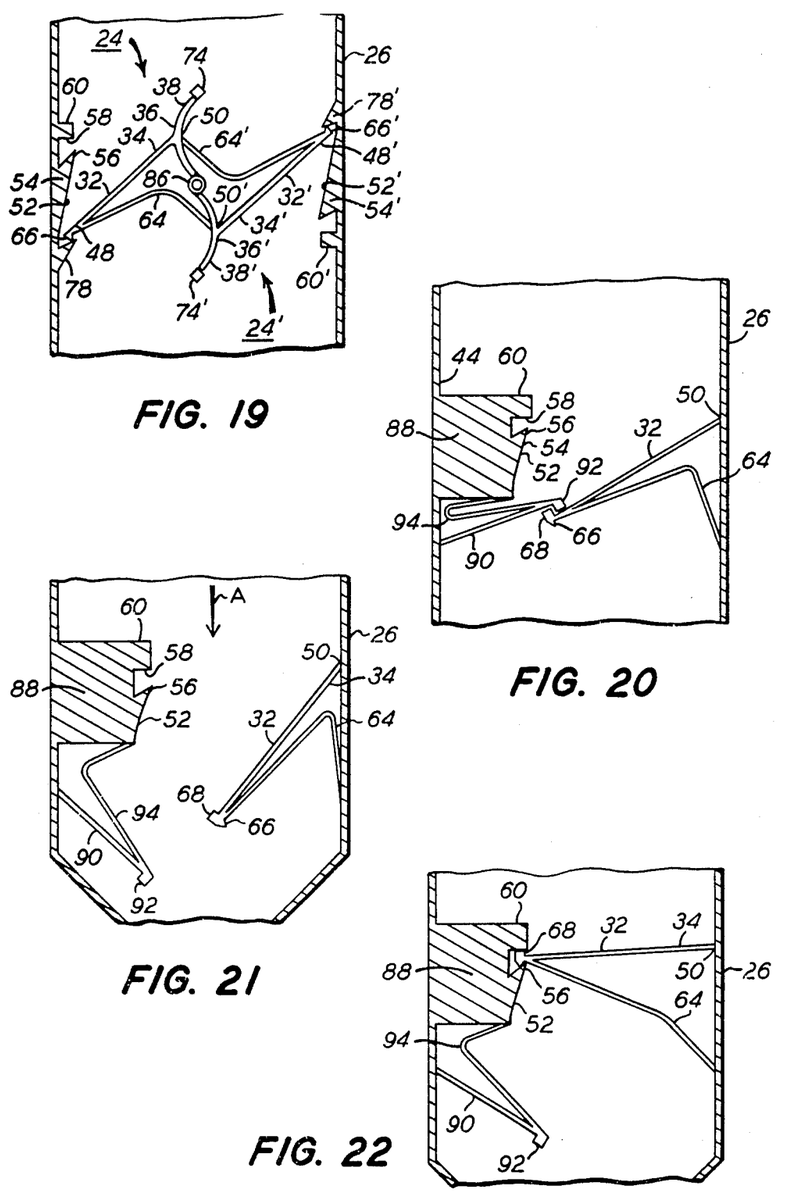
FIG. 19 is a segmental view similar to FIG. 15 in which the common mount for the over-center springs is rotatably movable with the over-center springs.
FIG. 20 is a segmental view in section of another embodiment of the valve means of this invention in which a lock means is provided for locking the main valve flap in its normal partially tensioned position.
FIG. 21 is a segmental view similar to FIG. 20 in which the lock means is released as the main valve flap is moved by the solution flow into its optimum tensioned position.
FIG. 22 is a segmental view similar to FIG. 20 in which the main valve flap is moved from its optimum tensioned position into its latched closed position.

With reference to FIG. 19, the dual valve means of FIGS. 15–17 is modified to incorporate catch members 78, 78' for free ends 48, 48' of main valve flaps 32, 32', and a rotatable post 86 to which one end of each of the first over-center springs 36, 36' is secured. The catch member 78, 78' hold free ends 48, 48' of valve flaps 32, 32' to assist in the inversion of the attached first over-center spring 36, 36'. The rotatable post 86 assists in the inversion of one of the first over-center springs 36, 36' upon inversion of the other first over-center springs 36, 36' due to movement of a selected one of the valve flaps 32, 32' into its latched closed position.

With reference to FIGS. 20, 21 and 22, another embodiment of the invention is disclosed in which main valve flap 32 has one end thereof pivotally secured directly to the inner wall 44 of valve chamber 26, instead of to an over-center spring 36. Catch and stop members 54, 60 respectively, are provided on one side surface of a block member 88 secured to the inner wall 44 of valve chamber 26. A lock means is provided for releasably locking the main valve flap 32 in its normal partially tensioned position, as seen in FIG. 20. The lock means comprises a valve plate 90 having one end pivotally secured to inner wall 44 of valve chamber 26, and its opposite end provided with a laterally extending lug 92 for engaging lip 68 on main valve flap 32. A fourth V-shaped leaf spring 94 has one end secured to the block member 88, and its opposite end secured to valve plate 90 for biasing valve plate lug 92 into engagement with lip 68 of valve flap 32 for releasably locking the main valve flap in its normal partially tensioned position. Accordingly, when the solution flow is initiated in the direction of arrow A, main valve flap 32 is moved from its normal partially tensioned position (FIG. 20), to its optimum tension position, shown in FIG. 21. Such movement releases valve plate 90, which moves into its extended position. When the solution flow is terminated, tensioned main valve flap 32 is returned or moved by its inherent tension or potential energy to its latched closed position, seen in FIG. 22.

Figure 23:
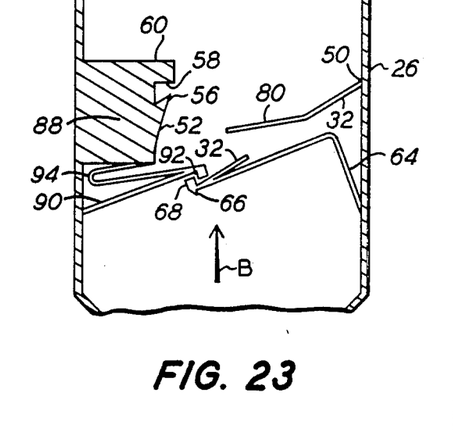
FIG. 23 is a segmental view similar to FIG. 20 in which the main valve flap is provided with a one-way flap valve for allowing solution flow in the opposite direction.
Figure 24:
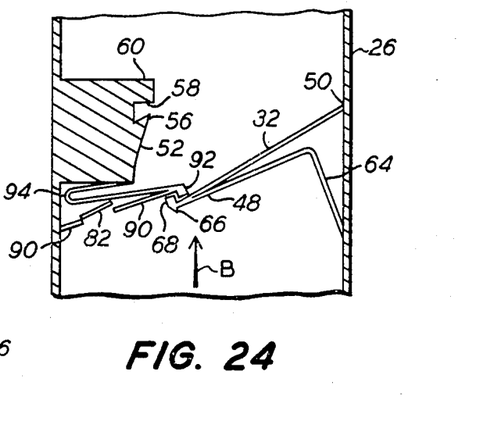
FIG. 24 is a segmental view similar to FIG. 23 in which the one-way flap valve is mounted in the lock plate of the lock means.
Figure 25:
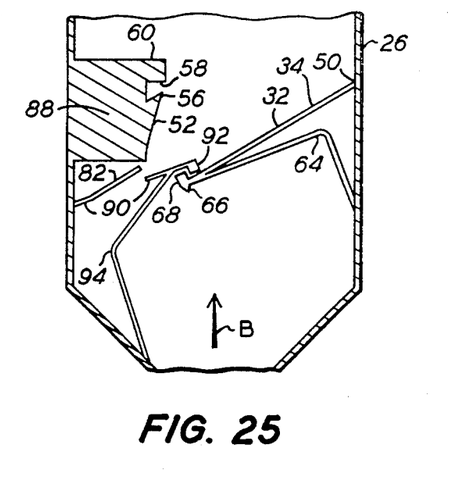
FIG. 25 is a segmental view similar to FIG. 24 showing another form of spring means for the lock plae of the lock means.

In FIG. 23, a modification of the invention disclosed in FIGS. 20–22 is disclosed in which main valve flap 32 is provided with a one-way flap valve 80 to allow solution flow in the direction of arrow B, no matter what position main valve flap 32 is in. In FIG. 24, the embodiment disclosed in FIGS. 20–22 is modified by providing a one-way flap valve 80 in valve plate 90. This embodiment of FIG. 24 is further modified in FIG. 25 by mounting fourth leaf spring 94 between valve plate 90 and inner wall 44 of valve chamber 26.

While preferred embodiments of the invention have been shown and described with particularity, it will be appreciated that various changes and modifications may suggest themselves to one having ordinary skill in the art, upon being apprised of the present invention. It is intended to encompass all such changes and modifications as fall within the scope and spirit of the appended claims.

What is claimed is:

1. A single flow valve for use in a hypodermic needle comprising:
    a valve chamber; and
    valve means mounted within the chamber for controlling solution flow through the chamber to a single-shot of solution in one direction, the valve means having an optimum tensioned position and a latched closed position and being movable to its optimum tensioned position in response to the flow of the single shot of solution through the valve chamber in the one direction, and movable to its latched closed position in response to its tensioned condition when the flow of solution is abated, whereby further solution flow in the one direction through the valve chamber is prevented.

2. A single-flow valve according to claim 1, wherein the valve means comprises a main valve flap having a normal position, the main valve flap being pivotal about one end and having an opposite free end, control means responsive to the force of the flow of solution for changing the position of the one end, the force of the flow of solution further moving the main valve flap to its optimum tensioned position, and latch means for latching the opposite end of the main valve flap in the latched closed position when the flow of solution is abated and the main valve flap is moved by the inherent tension therein from its tensioned position to its latched closed position.

3. A single-flow valve according to claim 2, wherein the valve means comprises means for mounting the one end of the main valve flap to the valve chamber, the mounting means comprising a first-over center leaf spring having a normal first over-center position, a second over-center position, and a mid-portion to which the one end is secured.

4. A single flow valve according to claim 3, wherein the control means comprises a cam member engageable by the free end of the valve flap which is and adapted upon initiation of the flow of solution to force the first over-center leaf spring to its second over-center position.

5. A single-flow valve according to claim 4, wherein the latch means comprises a stop member, and a catch member for guiding the free end of the valve flap into engagement with the stop member and capturing the free end between the stop and catch members.

6. A single flow valve according to claim 5, wherein the catch member has a ramp guide surface terminating in a tooth portion.

7. A single flow valve according to claim 6, wherein the free end of the main valve flap has a first laterally extending lip for engaging the tooth portion in the latched closed position of the main valve flap.

8. A single-flow valve according to claim 7, wherein the stop member has a groove therein, and the free end of the main valve flap has a second lip laterally extending in the opposite direction from the first lip for engagement with the stop member groove in the latched closed position of the main valve flap.

9. A single-flow valve according to claim 6, wherein the valve means comprises a second spring having one end connected to the main valve flap and the opposite end connected to the valve chamber for biasing the main valve flap toward its latched closed position.

10. A single-flow valve according to claim 9, wherein the second spring is a V-shaped leaf spring, and the valve chamber has a fixed support member to which the opposite end of the leaf spring is connected.

11. A single flow valve according to claim 4, wherein the control means further comprises a third over-center leaf spring coupled to the first over-center leaf spring and adapted upon initiation of the flow of solution to move over-center to assist movement of the first over-center spring to its second over-center position.

12. A single-flow valve according to claim 11, wherein the coupling between the first and third over-center leaf springs comprises a linking member.

13. A single flow valve according to claim 3, wherein one of the main valve flap and mounting means is provided with a one-way flap valve for allowing solution flow through the valve chamber in the opposite direction.

14. A single-flow valve according to claim 13, wherein the main valve flap is provided with a one-way flap valve for allowing solution flow through the valve chamber in the opposite direction, and means are provided for holding the one-way flap valve in a closed position when the main valve flap is moved to its latched closed position.

15. A single-flow valve according to claim 14, wherein the holding means comprises a fixed plate member on the valve chamber lying substantially in the plane of the main valve flap in its latched closed position.

16. A single-flow valve according to claim 1, wherein the valve means comprises substantially identical dual first and second valve means mounted within the valve chamber in 180° spaced relation for allowing solution flow in either direction only once, each of the first and second valve means comprising a main valve flap having a normal partially tensioned position, the main valve flap being pivotal about one end and having an opposite free end, control means responsive to the force of the flow of solution for changing the position of the one end of the main valve flap, the force of the flow of solution further moving the main valve flap to its optimum tensioned position, and latch means for latching the opposite end of the main valve flap in the latched closed position when the flow of solution is abated and the main valve flap is moved by the inherent tension therein from its tensioned position to its latched closed position.

17. A single-flow valve according to claim 16, wherein each of the first and second valve means comprises means for mounting the one end of the main valve flap to the valve chamber, the mounting means comprising a first over-center leaf spring having a normal first position, a second over-center position and a mid-portion to which the one end is secured.

18. A single-flow valve according to claim 17, wherein each of the first and second valve means comprises a second spring having one end connected to the main valve flap of one of the first and second valve means, and the opposite end of the second spring is connected to the mid-portion of the other of the first and second valve means.

19. A single-flow valve according to claim 17, wherein the control means comprises a cam member engageable by the free end of one of the main valve flaps which is and adapted upon initiation of the flow of solution to force one of the first over-center leaf springs to its second over-center position.

20. A single-flow valve according to claim 19, wherein each of the latch means comprises a stop member, and a catch member for guiding a free end of a main valve flap into engagement with the stop member, and capturing the free end between the stop and catch members.

21. A single-flow valve according to claim 20, wherein the catch member has a ramp guide surface terminating in a tooth portion.

22. A single-flow valve according to claim 17, wherein the first over-center leaf spring of each of the first and second valve means has a common support post on the valve chamber.

23. A single-flow valve according to claim 22, wherein the support post is rotatable upon movement of one of the first over-center leaf springs from its normal first position to its second position.

24. A single-flow valve according to claim 1, wherein the valve means comprises a main valve flap having a normal partially tensioned position intermediate, the optimum tensioned and latched closed positions, the main valve flap being pivotal about one end and having an opposite free end, lock means for releasably locking the main valve flap in the normal partially tensioned position, the lock means being released upon movement of the main valve flap to its optimum tensioned position in response to the solution flow, and latch means for latching the opposite end of the main valve flap in its latched closed position when the solution flow is abated and the main valve flap is moved by the inherent tension therein from its optimum tensioned position to its latched closed position.

25. A single-flow valve according to claim 24, wherein the lock means comprises a valve plate pivotally secured about one end to the valve chamber, and having a laterally extending lug on the opposite end of the valve plate, and a fourth spring having one end thereof secured to the valve chamber and the opposite end of the fourth spring secured to the valve plate for biasing the valve plate into engagement with the main valve flap.

26. A single-flow valve according to claim 25, wherein the main valve flap has a laterally extending lip at the opposite free end thereof, and the fourth spring comprises a V-shaped leaf spring having one end secured to the valve chamber and the opposite end thereof engageable with the valve plate for biasing the lug into locking engagement with the lip for releasably locking the main valve flap into its normal partially tensioned position.

27. A single-flow valve according to claim 24, wherein one of the main valve flap and valve plate is provided with a one-way flap valve for allowing solution flow through the valve chamber in a direction opposite to the one direction.

28. A single-flow valve according to claim 27, wherein the main valve flap is provided with a one-way flap valve for allowing solution flow through the valve chamber in the opposite direction, and means are provided for holding the one-way flap valve in a closed position when the main valve flap is moved to its latched closed position.

29. A single-flow valve according to claim 28, wherein the holding means comprises a fixed plate member mounted in the valve chamber and lying substantially in the plane of the main valve flap in its latched closed position.

30. A single-flow valve comprising:
a valve chamber;
valve means mounted within the valve chamber for movement between an open position in response to fluid flow through the valve chamber, and a latched closed position for at least substantially preventing fluid flow through the valve chambers;
latch means forming a part of the valve means for latching the valve means in the latched closed position; and
potential energy storing means forming a part of the valve means and responsive to the fluid flow through the valve chamber for storing potential energy for biasing the valve means to the latched closed position when the flow of fluid through the valve chamber is abated.

31. A single-flow valve according to claim 30, wherein the valve means comprises a main valve flap having a normal position, the main valve flap being pivotal about one end and having an opposite free end, control means responsive to the force of the flow of solution for changing the position of the one end, the force of the flow of solution further moving the main valve flap to its optimum tensioned position, and latch means for latching the opposite end of the main valve flap in the latched closed position when the flow of solution is abated and the main valve flap is moved by the inherent tension therein from its tensioned position to its latched closed position.

32. A single-flow valve according to claim 31, wherein the valve means comprises means for mounting the one end of the main valve flap to the valve chamber, the mounting means comprising a first-over center leaf spring having a normal first over-center position, a second over-center position, and a mid-portion to which the one end is secured.

33. A single flow valve according to claim 32, wherein the control means comprises a cam member engageable by the free end of the valve flap which is adapted upon initiation of the flow of solution to force the first over-center leaf spring to its second over-center position.

34. A single-flow valve according to claim 33, wherein the latch means comprises a stop member, and a catch member for guiding the free end of the valve flap into engagement with the stop member and capturing the free end between the stop and catch members.

35. A single flow valve according to claim 34, wherein the catch member has a ramp guide surface terminating in a tooth portion.

36. A single flow valve according to claim 35, wherein the free end of the main valve flap has a first laterally extending lip for engaging the tooth portion in the latched closed position of the main valve flap.

37. A single-flow valve according to claim 36, wherein the stop member has a groove therein, and the free end of the main valve flap has a second lip laterally extending in the opposite direction from the first lip for engagement with the stop member groove in the latched closed position of the main valve flap.

38. A single-flow valve according to claim 34, wherein the valve means comprises a second spring having one end connected to the main valve flap and the opposite end connected to the valve chamber for biasing the main valve flap toward its latched closed position.

39. A single-flow valve according to claim 38, wherein the second spring is a V-shaped leaf spring, and the valve chamber has a fixed support member to which the opposite end of the leaf spring is connected.

40. A single flow valve according to claim 33, wherein the control means further comprises a third over-center leaf spring coupled to the first over-center leaf spring and adapted upon initiation of the flow of solution to move over-center to assist movement of the first over-center spring to its second over-center position.

41. A single-flow valve according to claim 40, wherein the coupling between the first and third over-center leaf springs comprises a linking member.

42. A single flow valve according to claim 32, wherein one of the main valve flap and mounting means is provided with a one-way flap valve for allowing solution flow through the valve chamber in the opposite direction.

43. A single-flow valve according to claim 42, wherein the main valve flap is provided with a one-way flap valve for allowing solution flow through the valve chamber in the opposite direction, and means are provided for holding the one-way flap valve in a closed position when the main valve flap is moved to its latched closed position.

44. A single-flow valve according to claim 43, wherein the holding means comprises a fixed plate member on the valve chamber lying substantially in the plane of the main valve flap in its latched closed position.

* * * * *